United States Patent [19]

Naveh

[11] Patent Number: 5,891,847
[45] Date of Patent: Apr. 6, 1999

[54] TREATMENT OF DEGENERATIVE EYE DISORDERS

[75] Inventor: Nava Naveh, Tel Aviv, Israel

[73] Assignee: Ramot University Authority for Applied Research and Industrial Development Ltd., Tel-Aviv, Israel

[21] Appl. No.: 562,983

[22] Filed: Nov. 27, 1995

Related U.S. Application Data

[63] Continuation-in-part of Ser. No. 38,109, Mar. 29, 1993, abandoned.

[30] Foreign Application Priority Data

Apr. 1, 1992 [IL] Israel ......................................... 101441

[51] Int. Cl.⁶ .............................. A61K 38/00; C07K 5/00; C07K 16/00; C07K 17/00
[52] U.S. Cl. ................................. 514/12; 519/13; 519/14; 530/324; 530/326; 530/327; 530/312; 530/301
[58] Field of Search ..................................... 530/327, 326, 530/324, 312, 301; 514/13, 14, 12

[56] References Cited

U.S. PATENT DOCUMENTS 4,868,154 9/1989 Gilbard et al. ........................... 514/13

FOREIGN PATENT DOCUMENTS 0 145 113 6/1985 European Pat. Off. .
0 234 855 9/1987 European Pat. Off. .
3 623 019 1/1988 Germany .

OTHER PUBLICATIONS

T. Hanaoka, "Effect of Melanophore Hormone on Regeneration of Visual Purple in Solution", Nature, vol. 172, 1953, p. 866.

O.G. Stroeva, et al., "A Hormone–Sensitive Stage in Development of the Retinal Pigment Epithelium in the Hunter Rats with Inherited Retinal Distrophy", Ontogenez, vol. 19, No. 1, 1988, pp. 30–36.

Primary Examiner—Cecilia J. Tsang
Assistant Examiner—S. G. Marshall
Attorney, Agent, or Firm—Helfgott & Karas, P.C.

[57] ABSTRACT

Retinal dystrophies are treated by melanotropin peptides or analogs.

5 Claims, 6 Drawing Sheets

TREATMENT OF DEGENERATIVE EYE DISORDERS

This is a continuation-in-part to Ser. No. 08/038,109 filed on Mar. 29, 1993, now abandoned and claiming priority from Israel Patent Application No. 101441 of Apr. 1, 1992.

FIELD OF THE INVENTION

The present invention concerns treatment of degenerative eye disorders. More specifically, the present invention concerns the treatment of retinal photoreceptor dystrophies (RPD), age-related macular degeneration (AMD) and various retinal degenerations.

LIST OF PRIOR ART

The following is a list of prior art considered to be relevant as a background to the invention:

1. Levine, N., Sheftel, S. N., Eytan, T., Dorr, R. T., Hardley, M. E. and Weinrach, J. C., *JAMA*, 266:2730–2736.
2. Van der Neut, R., Bacer P. R., Sodaar, P., Gipsen, W. H., *Peptides*, 9:1015–1920 (1988).
3. Benelli, A., Zanoli, P., Botticelli, A. and Bertolini, A., *Eur. J. Pharmacol.*, 150:211–219 (1988).
4. Verhaagen, J., Edwords, P. M., Jennekens, F. G. I., Schotman, P. and Gipsen, W. H., *Exp Neurol.*, 92:451–454 (1986).
5. Hanaoka, T., *Nature*, 170:866, (1953).
6. Bauer, B. and Ehinger, B., *Acts. Physiol. Scand.*, 108:105–107 (1980).
7. Bar-Ilan, A. B., Savion, N., and Naveh, N., *Prostaglandins*, 43:31–43,(1992).
8. Stroeva, O. G. and Bibikova, A. D., *Ontogenez*, 19:30–36 (1988).
9. Leiba, H, Gatry, N. B., Schmidt, J., Piterman, O., Azrad, A., Salomon Y., *Eur. J. Pharmacol.*, 181:71–82, (1990).
10. Dayes, R. A., et al., *Journal of Immunology*, 139(1):103–109 (1987).
11. Eberle, A. N., (1988).
12. Sawyer, T. K., et al., *Peptides*, 11:351–357 (1990).
13. Johnston, M. F., Kravitz, E. A., Meiri, H. and Rahamimoff, *Science*, 220:1071–1072, (1983).
14. Hadley, Mac E., and Dawson, B. V., *Pigment Cell Research, Supplement* 1:69–78, (1988).
15. Faktorovich, E. G., Steinberg, R. H., Yasumura, D. and LaVail, M. M., *Neuro-ophthalmology*, 10:165–176.

The acknowledgement of these references herein do not amount to an admission that these references are relevant to the patentability of the invention as defined in the appended claims.

BACKGROUND OF THE INVENTION

RPD comprises a variety of genetically determined conditions, which differ from one another in their mode of inheritance, their pattern of visual loss and their clinical ophthalmological appearance. The spectrum of RPDs differ from one another also in their severity, the time of life in which they appear, the type of cells (rods or cones) which are affected, etc.

Another disorder of retinal dystrophy occurs late in life, and involves degenerative changes in the eye's retinal pigment epithelium (RPE), which is a highly pigmented epithelium underlying the retina resulting in photoreceptor and retinal degeneration. Such age-related degeneration occurs mainly in the macular area and will be referred to herein as "AMD" (age-related macular degeneration).

The macula is the area in the eye which enables the discern of small details and reading, and therefore degenerative changes in the macula cause visual impairment and even blindness. AMD in various degrees occurs in about 10% of subjects over 50 and about 30% of subjects over 75.

One of the main factors underlying AMD development is progressive deterioration of the metabolic activity of the RPE. One of the progressive deterioration of the metabolic activity of the RPE. One of the major roles of the RPE is to remove metabolic waste products generated in great abundance during the visual transduction activity of the overlaying retinal photoreceptor cells. AMD, furthermore develops as a result of the RPE's capacity to remove waste products and consequently they accumulate both within the cells and in the extracellular space which leads to a progressive destruction of the RPE cells. Destruction of the RPE cells is followed by progressive degeneration of the overlaying retina, leading eventually to impairment of vision and at times also to total blindness.

Although AMD is the most prevalent cause of blindness in the elderly population in developed countries, there is today no effective treatment available to prevent or delay the development of AMD.

Melanotropins are a group of peptides comprising $\alpha$-, $\beta$- and $\gamma$-melanocyte stimulating hormones (MSH). These are peptide hormones which are produced in the pituitary gland, and are a product of pro-opiomelanocortin, which is also a precursor of the adrenocorticotropic hormone (ACTH) and of $\beta$-endorphin. $\alpha$-MSH is a N-acetyl tridecapeptide (consisting of 13 amino acids) while $\beta$-and $\gamma$-MSH have 18 and 12 amino acids, respectively. Melanotropins and especially $\alpha$-MSH have been known for their role in regulation of the pigmentary system in vertebrates (Levine et al., 1991). $\alpha$-MSH has also been reported as having a number of biological activities including a neurotrophic effect on the growth of neural tissue both in the fetus and in the adult (Eberle, 1988, Ban der Neut, 1988) and stimulating regeneration of peripheral and spinal nerves (Van der Neut et al., 1988; Benelli et al., 1988; Verhagen et al., 1986).

Melanotropins have also been shown to affect skin tanning in humans and clinical trials (Phase I and Phase II) concerned with this indication of melanotropins are now being performed in the U.S.A.

Various effects of $\alpha$-MSH on the eye have hitherto been described. $\alpha$-MSH was found to accelerate the retinal visual purple regeneration in amphibians in vitro and in vivo and increases the sensitivity of these animals to light (Hanaoka, 1953); to increase release of neuro-transmitters, such as dopamine and GABA, from rabbit's retina in vitro (Bauer et al., 1980); to induce production of eicosanoid in cultured bovine RPE (Bar-Ilan et al., 1992); to increase protein synthesis in RPE of rats with hereditary retinal dystrophy (Stroeva et al., 1988); to have an effect on lacrimal glands, situated outside the eye, which possess receptors for $\alpha$-MSH (Leiba et al., 1990).

Derivatives of $\alpha$-MSH, in which one or more amino acids has been replaced by another have been described in the art. Some of these derivatives are more stable than the native peptide, and others such as Nle$^4$D-PHE$^7$ $\alpha$-MSH (SEQ ID NO: 4) were found to be even more potent than the native peptide in various biological effects (Dayes et al., 1987; Eberle, 1988). It is also known that only a few amino acids of $\alpha$-MSH are sufficient to bring about some of the biological activities of the native peptide (Sawyer et al., 1990).

SUMMARY OF THE INVENTION

The present invention provides a method for the treatment of retinal dystrophies and various degenerative disorders in an individual, comprising administering to the individual an effective amount of an active agent being a melanotropin peptide or an analog thereof, said analog being selected from the group consisting of agents which are capable of binding to melanotropin peptide receptors, agents capable of increasing the level of a second messenger of such receptors, and agents capable of mimicking or modulating the activation of the target of said second messenger.

An effective amount is an amount of the active agent which is effective in achieving the desired therapeutic effect. The effective amount depends on the administration regimen, the condition of the treated individual, etc. as known per se.

A particularly preferred indication of the method of the invention is in the treatment of age-related macular degeneration (AMD).

The active agents in accordance with the invention induce metabolic activation of the PRE cells. Accordingly, the melanotropin peptides and said analogs may be administered to an individual for treatment of disorders associated with depletions or other defects in the RPE cells which may be ameliorated by better metabolic activity of RPE.

Melanotropin peptides may be melanotropin ($\alpha$-MSH), $\beta$-MSH, $\gamma$-MSH, lipotropins of the $\beta$ (SEQ ID NO: 2) and $\gamma$ (SEQ ID NO: 3) type, etc.

The analogs of the melanotropin peptides comprise agents which are capable of binding to melanotropin peptides' receptors, agents capable of increasing the level of the second messenger of such receptors, e.g. activating the enzymatic pathway by which the second messenger is produced, they may be a permeable analog of the second messenger, or may also be s substance capable of mimicking or modulating the activation of the target of the second messenger.

Examples of the above analogs are derivatives of the melanotropin peptides which do not substantially reduce or at times increase the biological activity of the native peptide or increase duration of activity such as active fragments of melanotropin peptides (see Banelli et al., 1988, Johnston et al., 1983, and Hadley and Dawson 1988); melanotropin peptides or said fragments in which one or more amino acid has been deleted, replaced or chemically modified without substantially reducing the biological activity of the peptide or fragments thereof.

Currently preferred active agents in accordance with the invention include melanotropin, which is an N-acetyl-tridecapeptide having the sequenceofAc-Ser-Tyr-Ser-Met-Glu-His-Phe-Arg-Trp-Gly-Lys-Pro-Val-NH$_2$, (SEQ ID NO. 1) and analogs thereof. Examples of these analogs are peptides having a similar tertiary structure in the receptor-binding domain. A particular example of such an analog is Nle$^4$D-Phe$^7$ $\alpha$-MSH (SEQ ID NO: 4).

Analogs suitable for use in accordance with the invention may be selected based on their activity in inducing retinal preservation in various animal models of RPD such as in RCS rats (see example) below.

The active agent may be administered to individuals in a number or ways. By one mode of administration, said active agent is applied topically onto the eye. For topical application, said active agent may be formulated with a vehicle which is compatible with the eye and preferably such which facilitates penetration of said active agent into the eye. For such mode of application, said active agent may be formulated in the form of eyedrops (in which the active agent is dissolved in a physiological solution), in the form of ointments, in the form a liposome solution, etc.

Another mode of administration of said active agent is by periocular or intraocular injection. Periocular injection involves injection of the drug either into the conjuctiva or to the tennon (the fibrous tissue overlying the eye). In intraocular injection, said active agent is injected into the vitreous. Such injection may suitably by given, depending on the clinical status, once every three to six months. For such mode of administration, the active agent may be provided in an injection grade saline solution, in the form of an injectable liposome solution, etc.

Another, preferred mode of administration of said active agent is systemically. For systemic administration, the active agent may be given orally or administered parenterally or transdermally. For oral administration the active agent may be formulated in an edible liquid or solid food product, in the form of a pill or capsule, etc. For parenteral administration, the active agent may be formulated in a saline solution, in a liposome solution, etc.

In the following, the invention will be described with reference to some non-limiting examples with occasional reference to the annexed drawings.

EXAMPLE

Materials and Methods

Animals:

Royal College Surgeons (RCS) rats were used. In RCS rats, a progressive loss of photoreceptor cells, caused by a recessively autosomal mutation of the RPE (La Vail, 1981), leads to severe visual impairment. Due to the failure of pigment epithelium phagocytosis, rod outer segment material accumulates between the retina and the RPE and results in retinal degeneration. Photoreceptor degeneration in RCS rats was shown to begin at the 23rd postnatal day (p23) (Faktorovitch, 1990). The age of the animals in the experiment will hereinafter be referred to in relation with the postnatal day which will be indicated as pn, wherein n=the postnatal day. This disorder is similar to age-related macular degeneration in humans in that a metabolic insufficiency of the RPE cells results in a secondary progressive photoreceptor loss and vision impairment.

Preparation of histological sections:

Enucleated eyes removed from the orbit eyes were fixated for plastic embedding in epoxy resin (Faktorovitch 1990; La Vail, 1981). The eyes were sectioned parallel to the vertical meridian.

Morphometric evaluation of the histological sections:

The histological sections which were analyzed originated from the posterior part of the eye, from ora serata to ora serata including the optic nerve. Each histological preparation was analyzed by computerized image analysis. Twelve measurements (six from each side of the optic nerve) were taken at pre-determined points. At each point the number of rows of photoreceptors in the outer nuclear layer (ONL), as well as the thickness of inner plexiform layer (IPL) were determined.

Experimental Model:

The RCS rats of the experiment were divided into three groups of rats, each group including eight rats (8 eyes). The three groups were as follows:

1. RCS rats at the age of p23 receiving no treatment.
2. RCS rats at the age of p38 receiving no treatment.
3. RCS rats at the age of p23 receiving daily intramuscular injections to the hind leg containing α-MSH analog which was prepared as described above. Each rat received 0.01 micrograms of the α-MSH analog in 0.2 ml PBS in each injection.

The rats were sacrificed at the age of p38, the eyes were enucleated and then subjected to fixation and histological sections were prepared, as described above. The histological preparations of the eyes were examined morphometrically as described above and, in addition, the retinas were also examined by light microscopy.

Results:

Histological and morphometric analysis

Figure 1:
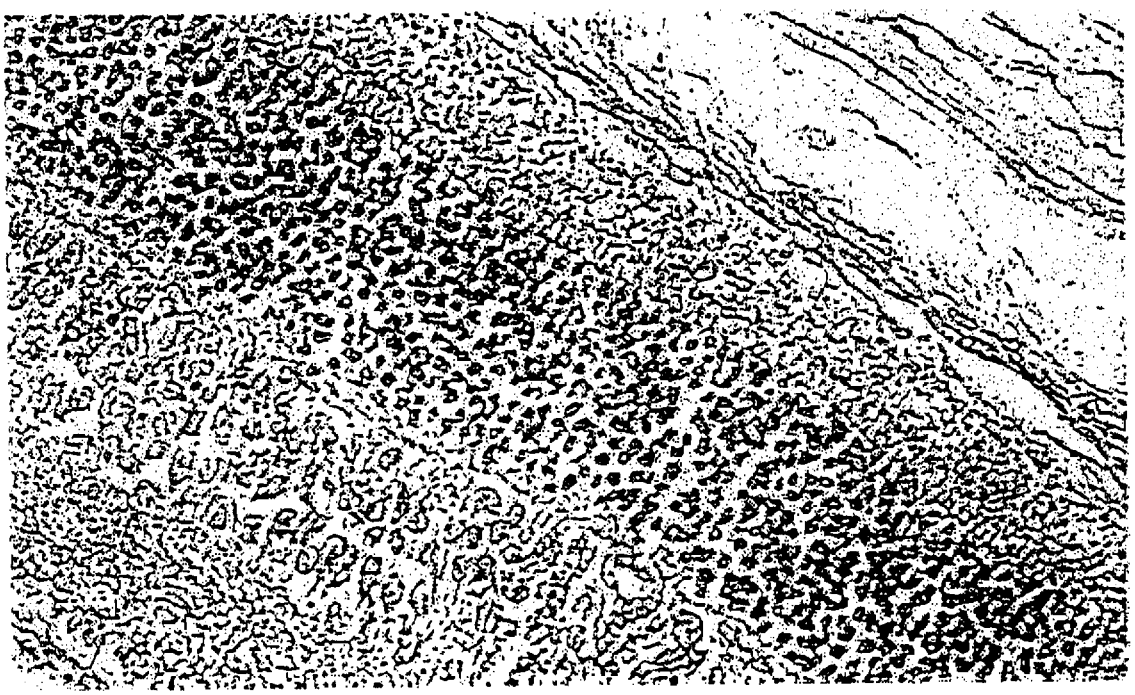
FIG. 1 shows a photograph of a histological preparation of a retina from a non-treated RCS rat at the age of p23 (Experimental Group No. 1)

As can be seen in FIG. 1, which shows a picture of a retina of an untreated RCS rat included in Group 1 of the experiment, at the age of p23, the retina contains an outer nuclear layer (ONL) which is comprised of 9–10 clearly defined rows of photoreceptors, and only a few degenerated cells are apparent. In addition, as can also be seen in the figure, the photoreceptor inner and outer segments are still visible although some debris material forming small clumps is evidenced in the outer segments.

Figure 2:
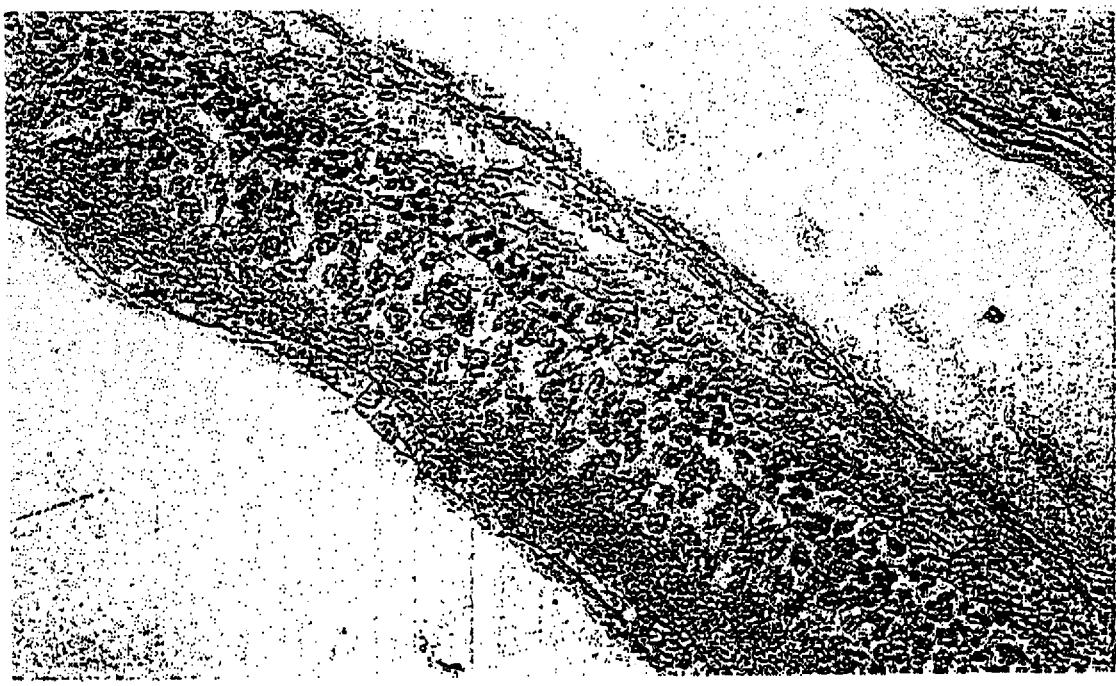
FIG. 2 shows a photograph of a histological preparation of a retina from a non-treated RCS rat at the age of p38 (Experimental Group No. 2)

As can be seen in FIG. 2, which is a photograph of a histological section of the retina of an untreated RCS rat at the age of p38, included in Experimental Group No. 2, the ONL is now comprised of only 3–4 rows of photoreceptors mostly showing cellular atrophy of varying degrees. As can be seen in the figure, the outer plexiform layer has disappeared and the photoreceptor inner and outer segments form clumps and no longer display the well defined organization which was observed in the same cells two weeks earlier, at the age of p23.

Figure 3:
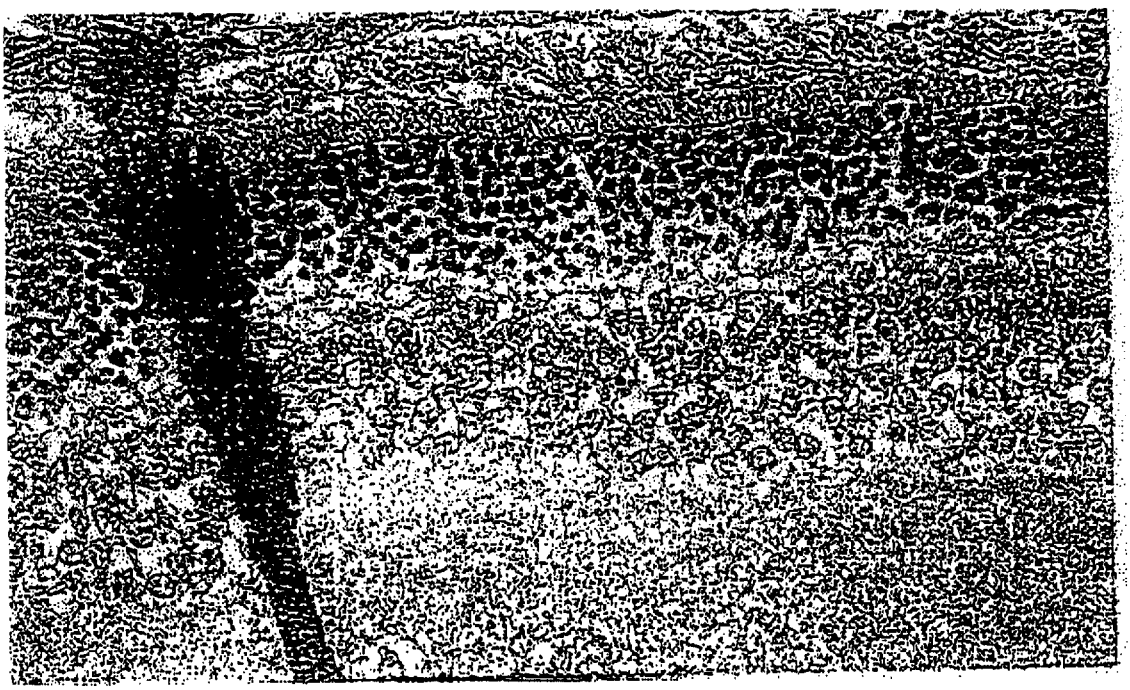
FIG. 3 shows a photograph of a histological preparation of a retina of an RCS rat at the age of p38 which received daily intramuscular injections of $\alpha$-MSH analog from the age of p23 to the age of p38 (Experimental Group No. 3)

Photoreceptors in the eyes of RCS rats treated with α-MSH analog were rescued from degeneration as compared to the degenerative changes observed in untreated RCS rats. This is apparent in FIG. 3, which is a photograph of a histological preparation of a retina of an RCS rat included in Experimental Group No. 3 which received daily injections of α-MSH analog as described above from the age of p23 to the age p38. As can be seen, the ONL of the retina of such a mouse is comprised of 7–8 layers of photoreceptors and the outer plexiform layer is still visible as compared to only 3–4 layers which are found in the untreated rats.

Quantitation of the effect of α-MSH analog treatment

The effect of α-MSH analog treatment on the retinas of the rats was quantitated by measuring the two following parameters at 11 or 14 points in the retina at various distances from the optic nerve:

1. The number of photoreceptor rows in the outer nuclear layer.
2. The thickness of the inner plexiform layer.

Figure 4:
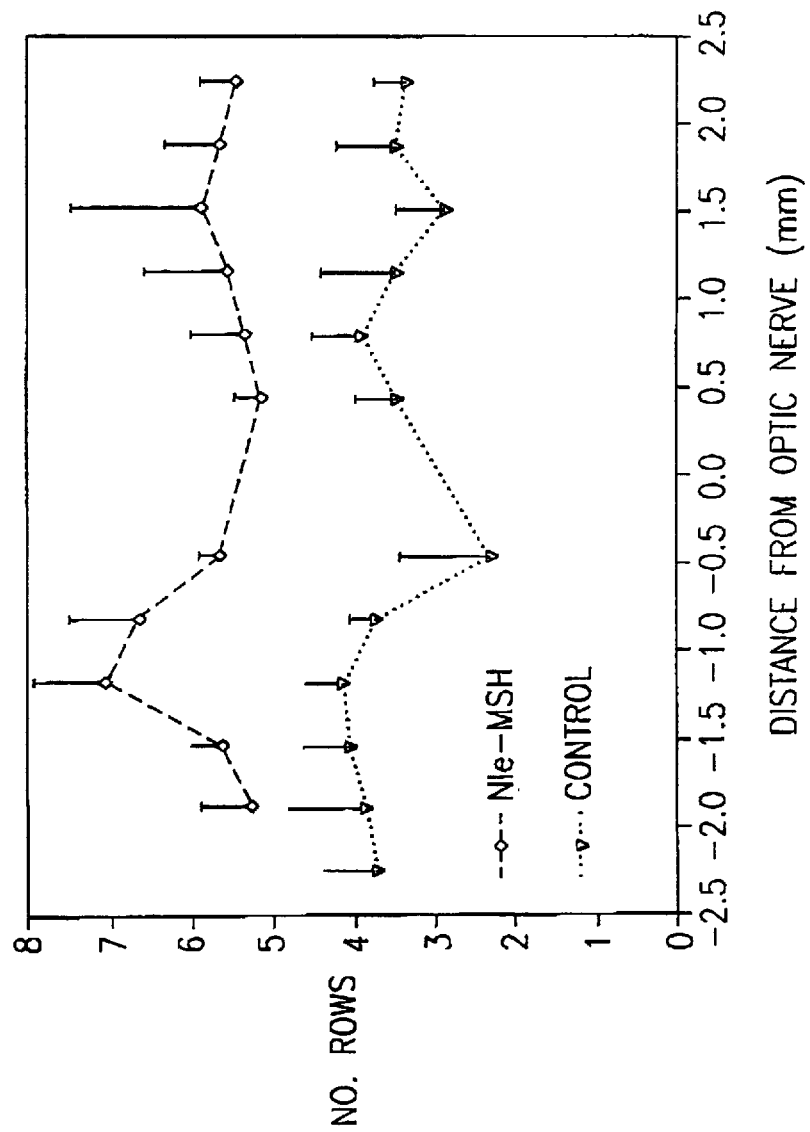
FIG. 4 shows the number of photoreceptor rows in the outer nuclear layer (ONL) of the retina of rats at the age of p38 which were either non-treated (Experimental Group No. 2) or treated with daily injections of $\alpha$-MSH analog (Experimental Group No. 3). The number of rows were analyzed in a number of locations in the retina which were at the different distances from the optic nerve.

1. Comparison of the number of photoreceptor rows in the ONL:

The effect of the α-MSH analog treatment to maintain a larger number of photoreceptors in the ONL was found to be significant as shown in FIG. 4. In this figure, the number of rows in the ONL of retinas of non-treated RCS rats on day p38 (Group 2 of the experiment) was compared to the number of photoreceptor rows in the ONL of retinas of RCS rats treated with the α-MSH analog (Group 3 of the experiment) in different areas of the retina. As can be seen in the figure, the mean number of photoreceptor rows in ONL of rats included in Group 1, was 5.6±0.6 (in 9 out of 11 points of measurement) as compared to the mean row number of 3.5±0.4 in ONL on non-treated rats of Group 2. The difference in the mean number of rows in the two groups of rats was significant ($p<0.05$ in Students T Test i.e., the mean row number in the treated mice was 60% higher than the mean number of rows in the α-MSH treated mice. As can be seen, the difference in the number of the non-treated and α-MSH treated rats was maximal in two points measured at the distance of 0.8 mm away from the optic nerve and 1.7 mm away from the optic nerve. At these two points, the number of rows of photoreceptors in the ONL of α-MSH treated mice (Group 3) was 2× higher than the number of photoreceptor rows in the ONL of non-treated mice (Group 2) ($p<0.001$ in Students T Test).

Figure 5:
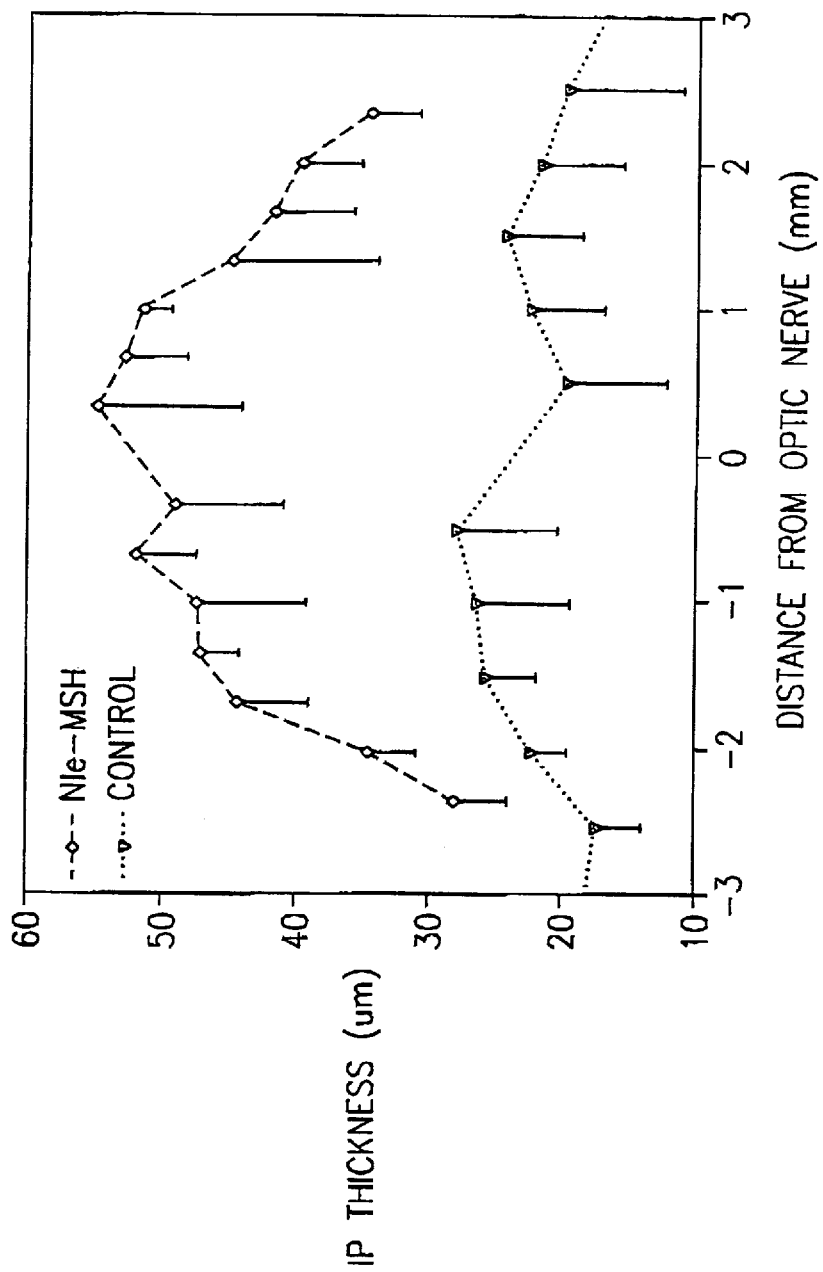
FIG. 5 shows the thickness of the inner plexiform layer (IPL) measured in several locations of the retina which were at different distances from the optic nerve in eyes of non-treated rats (Experimental Group No. 2) and in eyes of rats treated with the $\alpha$-MSH analogs (Experimental Group No. 3)

2. Thickness of the inner plexiform layer (IPL):

The thickness of the IPL at the age of p38 was measured in non-treated (Group 2) and α-MSH analog treated (Group 3) rat retinas. As can be seen in FIG. 5, the thickness of the IPL in the retina of rats treated with the α-MSH analog was significantly greater than the thickness of the IPL of untreated rats in all the points which were analyzed. At the central sector of the retina, spread 1.3 mm of each side of the optic nerve, the effect of the α-MSH analog treatment on the thickness of the IPL was most significant. As can be seen in the figure, the thickness of the IPL in the retina of the α-MSH treated rats was 50 microns as compared to only 23 microns in retinas of untreated rats. The difference between the thickness of the IPLs of the two above groups was statistically significant ($p<0.05$ in Students T Test).

Figure 6:
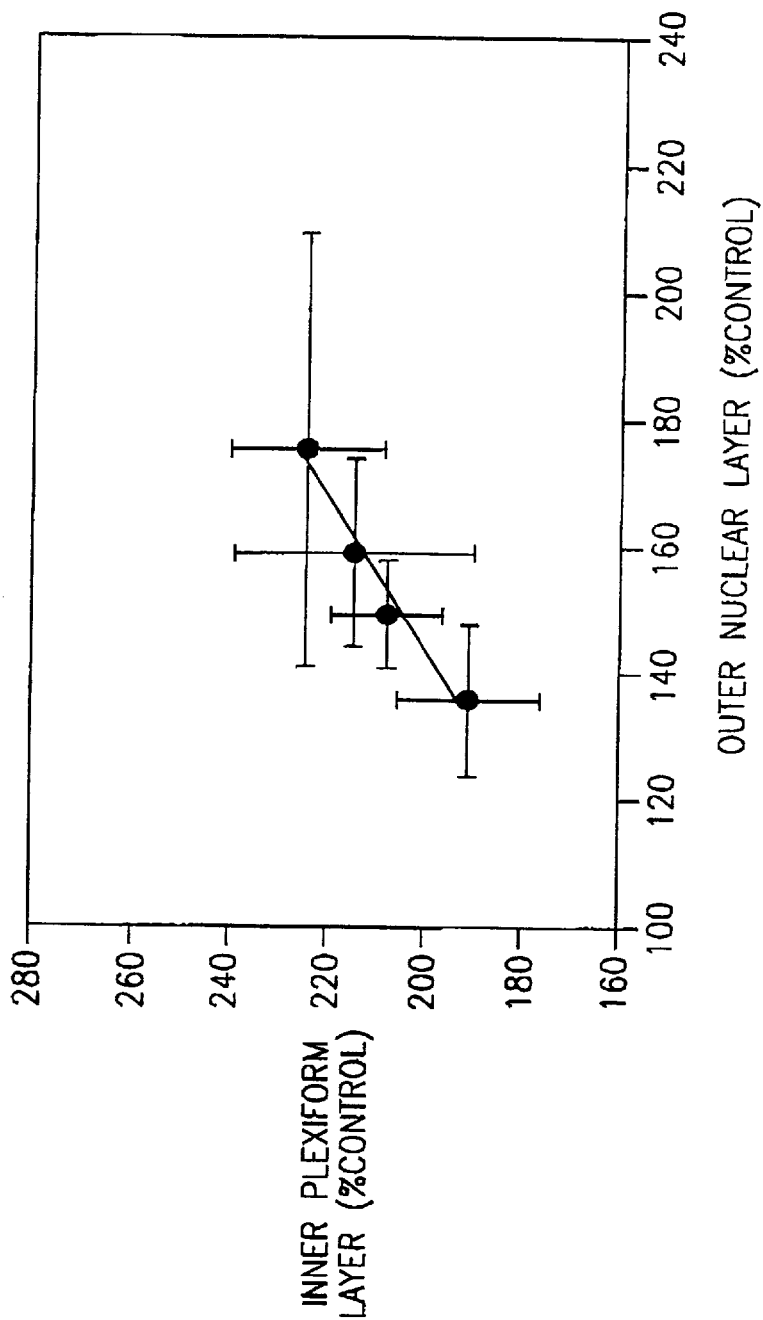
FIG. 6 shows the correlation between the number of photoreceptor layers in the retina of rats treated with $\alpha$-MSH analog (Experimental Group No. 3) and the thickness of the IPL in retinas of the same rats.

In order to analyze the correlation between the effect of the α-MSH analog treatment on the number of rows in the ONL of retinas of the treated rats to the effect of the α-MSH analogs on IPL thickness of the retinas of the same mice, regression line technique was used. As can be seen in FIG. 6, using this technique, it was shown that the effect of the α-MSH analog treatment on the number of photoreceptor rows in the ONL was directly correlated with the effect of α-MSH on the IPL thickness in the retinas of the rats ($r^2=0.96$).

Experiments using α-MSH:

An experiment similar to the one described above was also carried out in which the α-MSH analog treatment of Group 3 rats was replaced by α-MSH treatment. The result of this experiment, not shown were similar to the results of the above described experiment. Daily intramuscular injections of α-MSH to RCS rats, decreased degeneration of the photoreceptors and preserved the thickness of the adjacent retinal layers in retinas of treated rats as compared to retinas of non-treated rats. However, the efficacy of the α-MSH was less pronounced than that of the α-MSH analog used above, i.e. wherein 0.01–0.5 microgram of the α-MSH analog/rat were effective, 5–10 micrograms of the α-MSH were needed to obtain the same effect.

The above results clearly demonstrate that systemic administration of α-MSH and α-MSH analogs to RCS rats decreases the degeneration of the photoreceptors in the eye of RCS rats and maintains the thickness of the IPL.

---

I claim:

1. A method for the treatment of retinal dystrophies and various degenerative disorders in an individual, comprising administering to the individual an effective amount of an active agent being a melanotropin peptide or an analog thereof, said analog being selected from the group consisting of agents which are capable of binding to melanotropin peptide receptors, agents capable of increasing the level of a second messenger of such receptors, and agents capable of mimicking or modulating the activation of the target of said second messenger.

2. A method according to claim 1, where in the degenerative disorder is age-related macular degeneration.

3. A method according to claim 1, wherein said active agent is selected from the group consisting of melanotropin ($\alpha$-MSH), $\beta$-MSH, $\gamma$-MSH, $\beta$ (SEQ ID NO. 2) and $\gamma$ (SEQ ID NO:3) lipotropins and $Nle^4$D-$Phe^7$ $\alpha$-MSH.

4. A method according to claim 1, wherein said agent is administered topically to the eye.

5. A method according to claim 1, wherein said agent is administered systemically.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
  ( A ) LENGTH: 13 Amino Acids
  ( B ) TYPE: Amino Acid
  ( C ) STRANDEDNESS: Single
  ( D ) TOPOLOGY: Linear ( i i ) MOLECULE TYPE: Peptide ( i i i ) HYPOTHETICAL:

( i v ) ANTI-SENSE:

( v i ) ORIGINAL SOURCE:
  ( A ) ORGANISM:
  ( C ) INDIVIDUAL ISOLATE:
  ( G ) CELL TYPE:

( v i i ) IMMEDIATE SOURCE:
  ( A ) LIBRARY:
  ( B ) CLONE:

( x ) PUBLICATION INFORMATION:
  ( A ) AUTHORS:
  ( B ) TITLE:
  ( C ) JOURNAL:
  ( D ) VOLUME:
  ( E ) ISSUE:
  ( F ) PAGES:
  ( G ) DATE:
  ( K ) RELEVANT RESIDUES IN SEQ ID NO:

( x i ) SEQUENCE DESCRIPTION: SEQ ID NO: 1:

Ser Tyr Ser Met Glu His Phe Arg Trp Gly Lys Pro Val
1               5                       10

( 2 ) INFORMATION FOR SEQ ID NO: 2:

( i ) SEQUENCE CHARACTERISTICS:
  ( A ) LENGTH: 93 Amino Acids
  ( B ) TYPE: Amino Acid
  ( C ) STRANDEDNESS: Unknown
  ( D ) TOPOLOGY: Unknown ( i i ) MOLECULE TYPE: Peptide ( i i i ) HYPOTHETICAL:

( i v ) ANTI-SENSE:

( v i ) ORIGINAL SOURCE:
  ( A ) ORGANISM:
  ( C ) INDIVIDUAL ISOLATE:
  ( G ) CELL TYPE:

( v i i ) IMMEDIATE SOURCE:
  ( A ) LIBRARY:
  ( B ) CLONE:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( K ) RELEVANT RESIDUES IN SEQ ID NO:

( x i ) SEQUENCE DESCRIPTION: SEQ ID NO: 2:

```
Ser  Tyr  Ser  Met  Glu  His  Phe  Arg  Trp  Gly  Lys  Pro  Val  Gly  Lys  Lys
1              5                        10                       15

Arg  Arg  Pro  Val  Lys  Val  Tyr  Pro  Asn  Gly  Ala  Glu  Asp  Glu  Ser  Ala
               20                       25                  30

Glu  Ala  Phe  Pro  Leu  Glu  Phe  Lys  Arg  Glu  Leu  Thr  Gly  Gln  Arg  Leu
          35                       40                       45

Arg  Glu  Gly  Asp  Gly  Pro  Asp  Gly  Pro  Ala  Asp  Asp  Gly  Ala  Gly  Ala
     50                       55                       60

Gln  Ala  Asp  Leu  Glu  His  Ser  Leu  Leu  Val  Ala  Ala  Glu  Lys  Lys  Asp
65                       70                       75                       80

Glu  Gly  Pro  Tyr  Arg  Met  Glu  His  Phe  Arg  Trp  Gly  Ser
               85                       90
```

( 2 ) INFORMATION FOR SEQ ID NO: 3:

( i ) SEQUENCE CHARACTERISTICS:
        ( A ) LENGTH: 58 Amino Acids
        ( B ) TYPE: Amino Acid
        ( C ) STRANDEDNESS: Unknown
        ( D ) TOPOLOGY: Unknown ( i i ) MOLECULE TYPE: Peptide ( i i i ) HYPOTHETICAL:

( i v ) ANTI-SENSE:

( v i ) ORIGINAL SOURCE:
        ( A ) ORGANISM:
        ( C ) INDIVIDUAL ISOLATE:
        ( G ) CELL TYPE:

( v i i ) IMMEDIATE SOURCE:
        ( A ) LIBRARY:
        ( B ) CLONE:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( K ) RELEVANT RESIDUES IN SEQ ID NO:

( x i ) SEQUENCE DESCRIPTION: SEQ ID NO: 3:

```
Ser  Tyr  Ser  Met  Glu  His  Phe  Arg  Trp  Gly  Lys  Pro  Val  Gly  Lys  Lys
1              5                        10                       15

Arg  Arg  Pro  Val  Lys  Val  Tyr  Pro  Asn  Gly  Ala  Glu  Asp  Glu  Ser  Ala
               20                       25                  30

Glu  Ala  Phe  Pro  Leu  Glu  Phe  Lys  Arg  Glu  Leu  Thr  Gly  Gln  Arg  Leu
          35                       40                       45

Arg  Glu  Gly  Asp  Gly  Pro  Asp  Gly  Pro  Ala
     50                       55
```

( 2 ) INFORMATION FOR SEQ ID NO: 4:

```
    (  i  ) SEQUENCE CHARACTERISTICS:
            ( A ) LENGTH: 13 Amino Acids
            ( B ) TYPE: Amino Acid
            ( C ) STRANDEDNESS: Single
            ( D ) TOPOLOGY: Linear (  i i  ) MOLECULE TYPE: Peptide (  i i i  ) HYPOTHETICAL:

(  i v  ) ANTI-SENSE:

(  v i  ) ORIGINAL SOURCE:
            ( A ) ORGANISM:
            ( C ) INDIVIDUAL ISOLATE:
            ( G ) CELL TYPE:

(  v i i  ) IMMEDIATE SOURCE:
            ( A ) LIBRARY:
            ( B ) CLONE:

(  x  ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( K ) RELEVANT RESIDUES IN SEQ ID NO:

(  x i  ) SEQUENCE DESCRIPTION: SEQ ID NO: 4:

Ser   Tyr   Ser   Xaa   Glu   His   Phe   Arg   Trp   Gly   Lys   Pro   Val
1                       5                             10
```